(12) United States Patent
Yerazunis

(10) Patent No.: US 7,170,606 B2
(45) Date of Patent: Jan. 30, 2007

(54) MULTI-WAY LED-BASED SURFACE REFLECTANCE SENSOR AND SPECTROPHOTOMETER

(75) Inventor: William S. Yerazunis, Acton, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 503 days.

(21) Appl. No.: 10/802,501

(22) Filed: Mar. 17, 2004

(65) Prior Publication Data

US 2004/0247484 A1    Dec. 9, 2004

Related U.S. Application Data

(63) Continuation-in-part of application No. 10/251,251, filed on Sep. 20, 2002, now Pat. No. 7,008,795.

(51) Int. Cl.
| | |
|---|---|
| G01N 21/00 | (2006.01) |
| G01J 1/00 | (2006.01) |
| C12Q 1/68 | (2006.01) |
| H01J 43/00 | (2006.01) |
| G01B 11/24 | (2006.01) |
| G01J 1/44 | (2006.01) |

(52) U.S. Cl. ............... 356/432; 356/213; 356/612; 250/200; 250/214 R; 250/214 LA; 250/227.21

(58) Field of Classification Search ............ 356/39, 356/612, 213, 432; 422/82, 82.05; 250/214 R, 250/214 LA See application file for complete search history.

(56) References Cited

U.S. PATENT DOCUMENTS

| | | | | |
|---|---|---|---|---|
| 3,818,451 | A * | 6/1974 | Coleman | ............ 326/104 |
| 3,910,701 | A * | 10/1975 | Henderson et al. | ............ 356/39 |
| 4,622,477 | A * | 11/1986 | Uda | ............ 327/109 |
| 4,848,901 | A * | 7/1989 | Hood, Jr. | ............ 356/41 |
| 5,073,029 | A * | 12/1991 | Eberly et al. | ............ 356/432 |
| 5,149,962 | A * | 9/1992 | Maurice | ............ 250/227.17 |
| 5,268,635 | A * | 12/1993 | Bortolini et al. | ............ 324/96 |
| 5,408,092 | A * | 4/1995 | Maurice et al. | ............ 250/227.21 |
| 5,631,757 | A * | 5/1997 | Bodeep et al. | ............ 398/138 |
| 6,396,614 | B1 * | 5/2002 | Yoshizawa | ............ 398/202 |
| 6,701,091 | B2 * | 3/2004 | Escobosa et al. | ............ 398/107 |

OTHER PUBLICATIONS

U.S. Appl. No. 10/126,761, filed Apr. 19, 2002, Dietz et al.

* cited by examiner

*Primary Examiner*—Jill Warden
*Assistant Examiner*—Nell Turk
(74) *Attorney, Agent, or Firm*—Dirk Brinkman; Clifton D. Mueller; Gene V. Vinokur

(57) ABSTRACT

A light sensor circuit based on direct connection of LEDs to I/O pins of a microcontroller. The LEDs are reverse biased and the parasitic junction capacitance is charged in an output mode. Then, the I/O pins placed into an high-impedance input mode. The time for the capacitance to be discharged by photoconduction caused by light incident on the LEDs is inversely proportional to an intensity of the incident light, and can be directly measured as the time required for the I/O pin to transition from fully-charged (5 volts) to a logic threshold level (1.7 volts). By using multiple LEDs, multiplexed between emissive and sensing modes, a wide variety of sensors can be constructed, particularly, when the LEDs emit light at different wavelength.

39 Claims, 9 Drawing Sheets

100

200

MULTI-WAY LED-BASED SURFACE REFLECTANCE SENSOR AND SPECTROPHOTOMETER

RELATED APPLICATION

This application is a Continuation-in-Part Application of U.S. patent application Ser. No. 10/251,251, titled "Multi-Way LED-Based Chemochromic Sensor," filed by Yerazunis et al. on Sep. 20, 2002 now U.S. Pat. No. 7,008,795.

FIELD OF THE INVENTION

This invention relates generally to surface reflectance sensors and more particularly to LED-based surface reflectance sensors and spectrophotometers

BACKGROUND OF THE INVENTION

With a surface reflectance sensing system, a material to be tested is illuminated by a light source, and reflected light is measured with a light sensor. The light can be monochromatic, a range of wavelengths, or a mixture of wavelengths, such as 'white' light. This can be accomplished either by filtering the emitted light or the sensed light.

For example, the light source can be a wide-band tungsten-halogen or a tungsten-deuterium light that is filtered. The filtered light is transmitted to the surface, and then reflected and carried back to a sensor via an optical fiber. The wavelengths can be separated by a slit and diffraction grating, and measured by a photodiode array or CCD array and an analog-to-digital (A/D) converter. Depending on a width of the slit and a fineness of the diffraction grating, a resolution of 1 to 4 nanometers can be attained across a range of 350 to 1100 nanometers. There, the A/D converter is the most expensive component of the system.

In another surface reflectance system, narrow-band LEDs are used to emit light at known wavelengths, and photodiodes and an A/D circuit are used to measure the reflected light. Although, that type of system is less expensive, the small number of available colors available, e.g., five, makes it less suitable for analytical work.

LED-based systems have been used for color matching in the graphic arts, printing, photocopying, publishing, and paint-matching trades.

All of the prior art systems use conventional A/D circuits. In such circuits, the phototransistor or photodiode is a light-controlled current source or light-controlled resistor. The current generated by the photodiode device is amplified and directly measured by the A/D converter. Because the directly measured instantaneous current is typically only a few microamperes, a sensitive, low-noise amplifier must be used. That substantially increases the expense, size and power requirements of the system.

In addition, silicon photodiodes have a peak sensitivity at roughly 670 to 700 nanometers, extending into deep infrared, and are relatively insensitive to blue and ultraviolet light. Therefore, a proportional filter is used to 'flatten' the response to match that of the human eye, which decreases the sensitivity of the system. Furthermore, the dynamic range of a conventional 16-bit converter is roughly 64,000:1, with a considerable power consumption.

Therefore, there is a need for surface reflectance sensors and spectrophotometers that overcome the problems of the prior art.

SUMMARY OF THE INVENTION

The present invention provides an inexpensive surface reflectance sensing system with a high dynamic range, and a low power requirement. The system is particularly suited for applications where there is a minimal amount of light.

The invention replaces the prior art amplifier and A/D converter with a simple thresholding circuit. In this circuit, pairs of photodiodes, preferably LEDs, are directly connected to corresponding digital input/output (I/O) pins of a microcontroller, which is controlled by software.

Current delivered by the I/O pins set the cathode of the LED to a logical 1, nominally +5 volts for TTL compatible parts, and the anode to a logical 0, i.e., 0 volts. One photodiode emits light onto a surface of a material to be tested when switched in a forward bias state, while the other photodiode senses reflected light when first charged in a reverse bias state, and then allowed to discharge.

In the reverse bias state, an internal parasitic junction capacitance of the LED is charged. The junction capacitance varies, on the order of 20 picofarads. The imposed voltage is due to the varactor effect. The parasitic capacitance can also include capacitance inherent in the microcontroller I/O pins and connective wiring. Assuming a capacitance of 20 pFarads and 5 volts, approximately 100 picoCoulombs of charge is stored in the junction.

After the junction capacitor is fully charged, which takes only a few microseconds, the microcontroller I/O pin is switched to a high impedance input state, e.g., one million Ohms to 250 giga-Ohms. Even in this high-impedance state, the I/O pin can still be 'read' by the software. If the voltage on the I/O pin is greater than a predetermined logic threshold voltage, e.g., +1.7 volts, then the input at the pin is read as a logical '1', and otherwise, the input is read as a logical '0'. In the high-impedance mode, it takes several seconds to discharge the 20 picofarad LED junction capacitance from +5 volts down to the digital logic threshold of 1.7 volts when the current drain is minimal, that is, absent the presence of incident light. In full sunlight, the current drain can be on the order of one microampere.

A polling program or an interrupt service procedure in the microcontroller can measure the amount of time it takes to discharge the junction from +5 volts down to the threshold voltage of 1.7 volts. This time is inversely proportional to the amount of incident light. In bright light, e.g., direct sunlight, the discharge takes only a few microseconds. In a moderately lit environment, the discharge takes about 100 milliseconds, and under minimal lighting, the discharge can take several seconds.

The very wide dynamic range of the sensor system according to the invention, i.e., several million to one, greatly exceeds the dynamic range of any prior art surface reflectance sensors that use amplifiers and A/D converters.

As an advantage, an LED is generally equally sensitive to all wavelengths equal or shorter than an emission wavelength of the LED. Light at longer wavelengths generates significantly less photocurrent. For example, a yellow LED responds almost equally well to yellow, green, blue light, and ultraviolet light, but does not respond to orange, red, or infrared light. Therefore, a very inexpensive coarse-resolution spectrograph can be constructed by using concurrently several LEDs tuned to different colors.

In this embodiment, each LED sensor responds only to wavelengths equal to or shorter than the emission wavelength of the sensor. Thus, it is possible to reconstruct the per-band light intensities, or spectra, of the incident light.

As an additional advantage, the LEDs can be switched rapidly between emitting and sensing modes. In this way, longer-wavelength LEDs can be used both as sensors for shorter wavelength LEDs, as well as emitters for yet longer wavelength LEDs. In this configuration, material to be tested reflects emitted light to one or more sensor LEDs. Thus, the LEDs can operate as narrow-band emitters and as a high-pass sensor using the same circuit.

As another advantage, a filtering element, such as a UV-blocking filter, can be added so that the system operates as a fluorescence sensor. In this embodiment, a widest-band-sensitivity LED is used, e.g., a red or infrared LED, which can sense respectively all visible light, or all visible and near infrared wavelengths. More than one LED can be used with the UV-blocking filter to provide a coarse resolution fluorescence spectrograph.

This configuration, where a short-wave-blocking filter covers one or more of the sensing LEDs, can detect the presence or absence of small amounts of a material that may fluoresce in either the visible or infrared wavelength ranges.

As another advantage, the LEDs can be switched rapidly between emitting and sensing modes, e.g., less than a microsecond. In this way, differential measurements can be acquired, where the sensor measures transmitted or reflected light in both the presence and absence of an excitation source, and the actual useful signal is a difference function of the two signals.

DETAILED DESCRIPTION OF THE PREFERRED EMBODIMENT

Basic Bi-Directional LED Sensor Circuit

Figure 1:
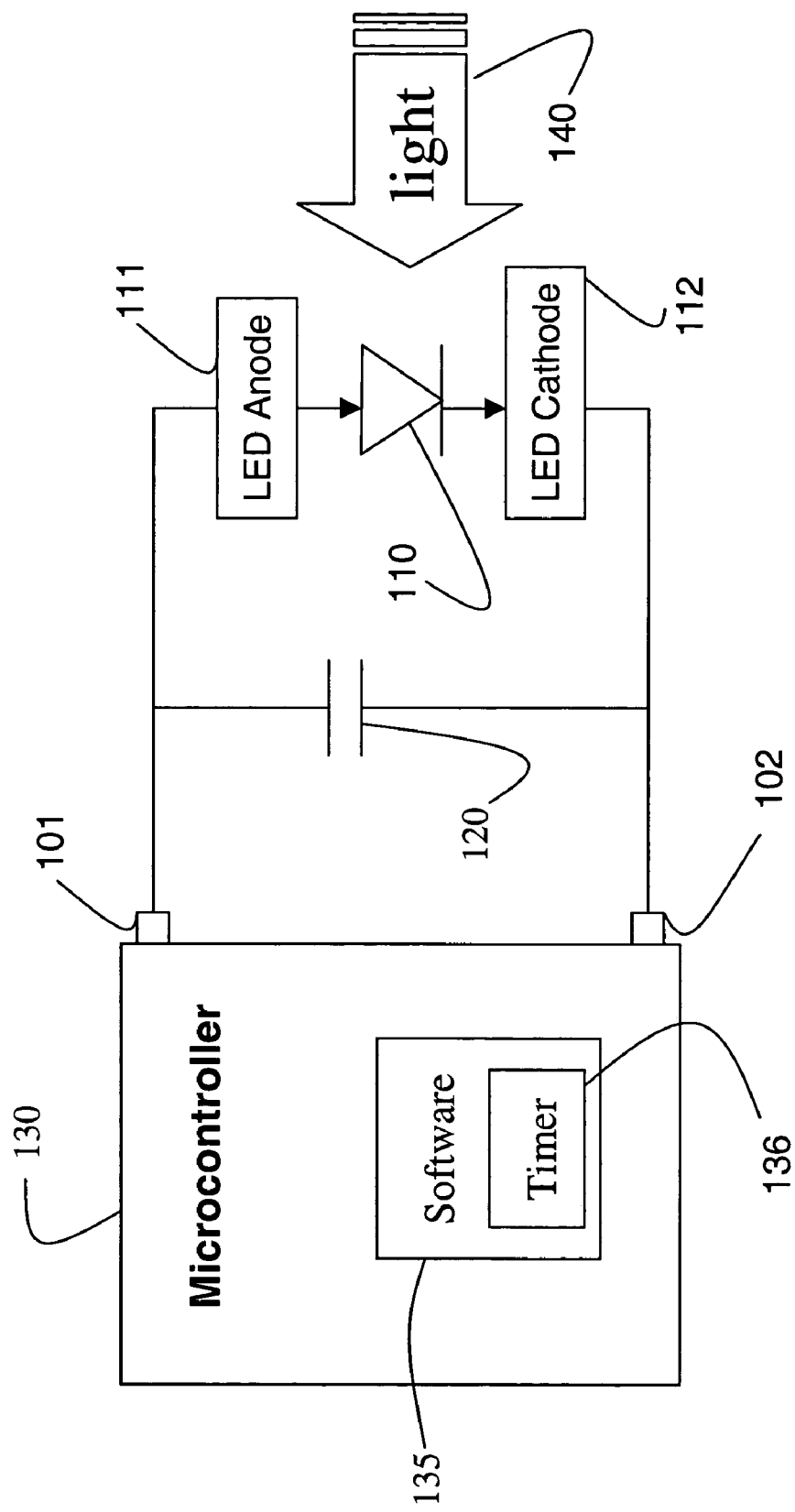
FIG. 1 is a block diagram of a light sensor with a single LED according to the invention.

FIG. 1 shows an LED-based light sensor 100 according to the invention. The sensor includes an LED 110, a capacitor 120, and a microcontroller 130. An anode 111 of the LED 110 is connected to a bi-directional digital I/O pin 101 of the microcontroller. A cathode 112 is connected to another pin 102. The state of current on the I/O pins 101–102 determines whether the LED 110 emits or senses light. For a detailed description of light emitting diodes operating as both an emitter and a sensor see U.S. patent application Ser. No. 10/126,761 "Communication Using Bi-Directional LEDs," filed by Dietz et al. on Apr. 19, 2002, incorporated herein by reference in its entirety.

The microcontroller 130 can be a MicroCircuits Inc. PIC 16F876 processor, which as multiple data pins. The microcontroller 100 also has conventional power and communication connections. These connections are not shown for clarity. The microcontroller can execute software 135.

In addition, to operate LEDs as described herein, the software also performs timing functions (timer) 136 by either a polling procedure, an interrupt service procedure, or using a clock. The timing function essentially measures the amount of time it takes to discharge capacitance stored in the LEDs by an induced photocurrent. The amount of time is inversely proportional to the intensity of incident light. In the embodiment of the invention where multiple LEDs are used, as described herein, the timer can make these timing measurements in parallel or serially.

When microcontroller pin 101 connected to LED anode 111 is configured as an output at Logic 1 (5.0 volts), and microcontroller pin 102 connected to LED cathode pin 112 is configured as an output at Logic 1 (0.0 volts) the LED emits light. The current in this circuit is limited by the output drive capability of the microcontroller output pin. This is a small deviation from common practice in that common practice connects the LED cathode pin 112 to a microcontroller pin but connects the anode 111 to +5 volts either directly or through a current-limiting resistor, typically 220 ohms. The conventional practice is to connect the LED anode pin 111 to microcontroller pin 101, but connects the LED cathode pin 102 directly to ground.

The advantage of the circuit 100 is that by configuring microcontroller pin 101 (connected to LED anode 111) an output at logic 0 (grounded), and configuring microcontroller pin 102 (connected to LED cathode 112) as an output at logic 1 (+5.0 volts), the LED 100 is reverse-biased. This does not cause a significant current, but it does charge the parasitic junction capacitance of the LED 110. This parasitic capacitance is typically on the order of 20 picofarads.

After the parasitic capacitance of LED 110 is charged, typically in a few tens of microseconds, the microcontroller pin 102 connected to LED cathode 112 is reconfigured from output mode to input mode. In input mode, the resistance of microcontroller pin 102 to ground is on the order of a million million ohms, i.e., one million mega ohms. In this state, software can read the logic state of pin 102. If the voltage is greater than the logic threshold of the system, e.g., +1.7 volts for TTL-compatible microcontrollers, then the software 135 reads the logic value "1", otherwise, the software reads the logic value 0.

As time passes, the charge stored on the parasitic capacitance of the LED 110 dissipates slowly. By far, the greatest cause for this dissipation is incident light 140 striking the junction of LED 110. The parasitic capacitance of the LED connected as described above can hold charge above the 1.7 volt logic level for several seconds in a darkened room, but for only a few microseconds when exposed to direct sunlight. Intermediate amounts of light caused intermediate time-to-discharge time durations.

The software 135 is then used to measure the time for the LED 110 to discharge from +5 volts down to the logic threshold at 1.7 volts. By determining the width of the logic 1 pulse, the software can determine an intensity of the light striking LED 110.

Therefore, the circuit in FIG. 1 can be operated to directly produce a pulse-width-modulated logic-level signal with the pulse width inversely proportional to the intensity of light 140. This pulse width can be measured by the microcontroller to yield a numerical representation of the intensity of the light 140. Note that at no time is an analog-to-digital converter employed. Note also that the duration of time measurement is the determining factor of the resolution of the system. It should also be noted that because the photocurrent discharging LED 110 is the major source of current drain in the system, the circuit shown in FIG. 1 actually integrates the light falling onto LED 110. Integration of light produces a much greater sensitivity than the instantaneous measurements of the prior art.

In the rare instance where the light incident on the LED 110 is so bright that the decay time is too short for convenient measurement by the microcontroller, an additional capacitor 120 can be added to the circuit to increase the charge to be discharged, thereby lengthening the time required to measure the discharge. In normal use the capacitor 120 is unnecessary, and the internal parasitic capacitance of LED 110 is adequate for correct operation of the system.

Multiple Sensors

Figure 2:
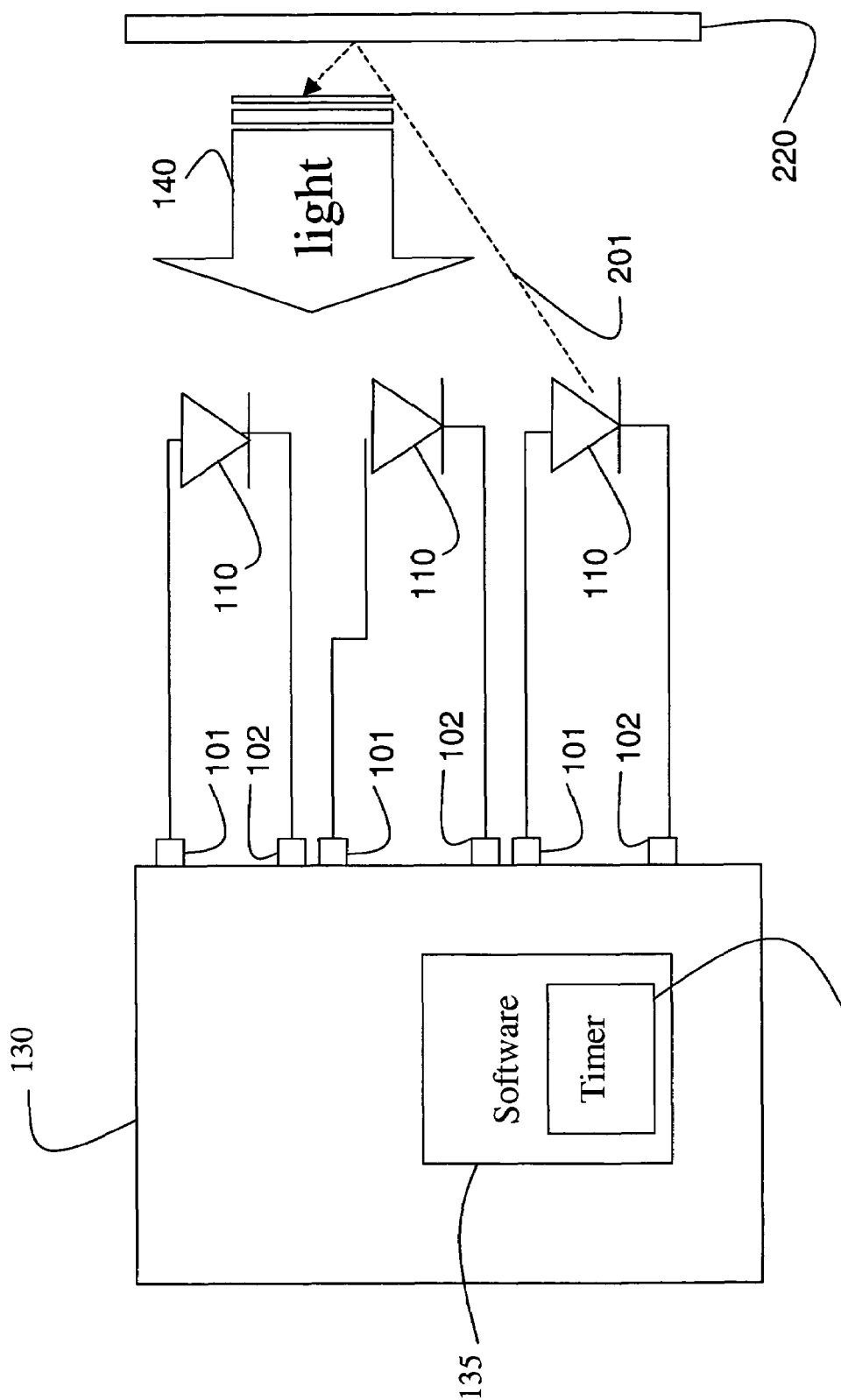
FIG. 2 is a block diagram of a multiple LED light sensor according to the invention.

FIG. 2 shows an LED-based reflectometer 200 according to the invention. In this configuration, the microcontroller 130 is connected to a set of LEDs 110 via multiple pairs of pins 101–102 to measure the light reflectance of a surface 220 under test. Each LEDs is separately controllable to either emit or sense light, or to be inactive. Thus, a first subset of the LEDs, i.e., one or more, can emit light, while a second subset, i.e., one or more, senses light emitted by the first subset. In this embodiment, the LEDs can be tuned to different wavelengths, so that not all of the wavelengths are identical, and the sensing can be done serially or in parallel.

Sensing Reflected Light

Figure 3:
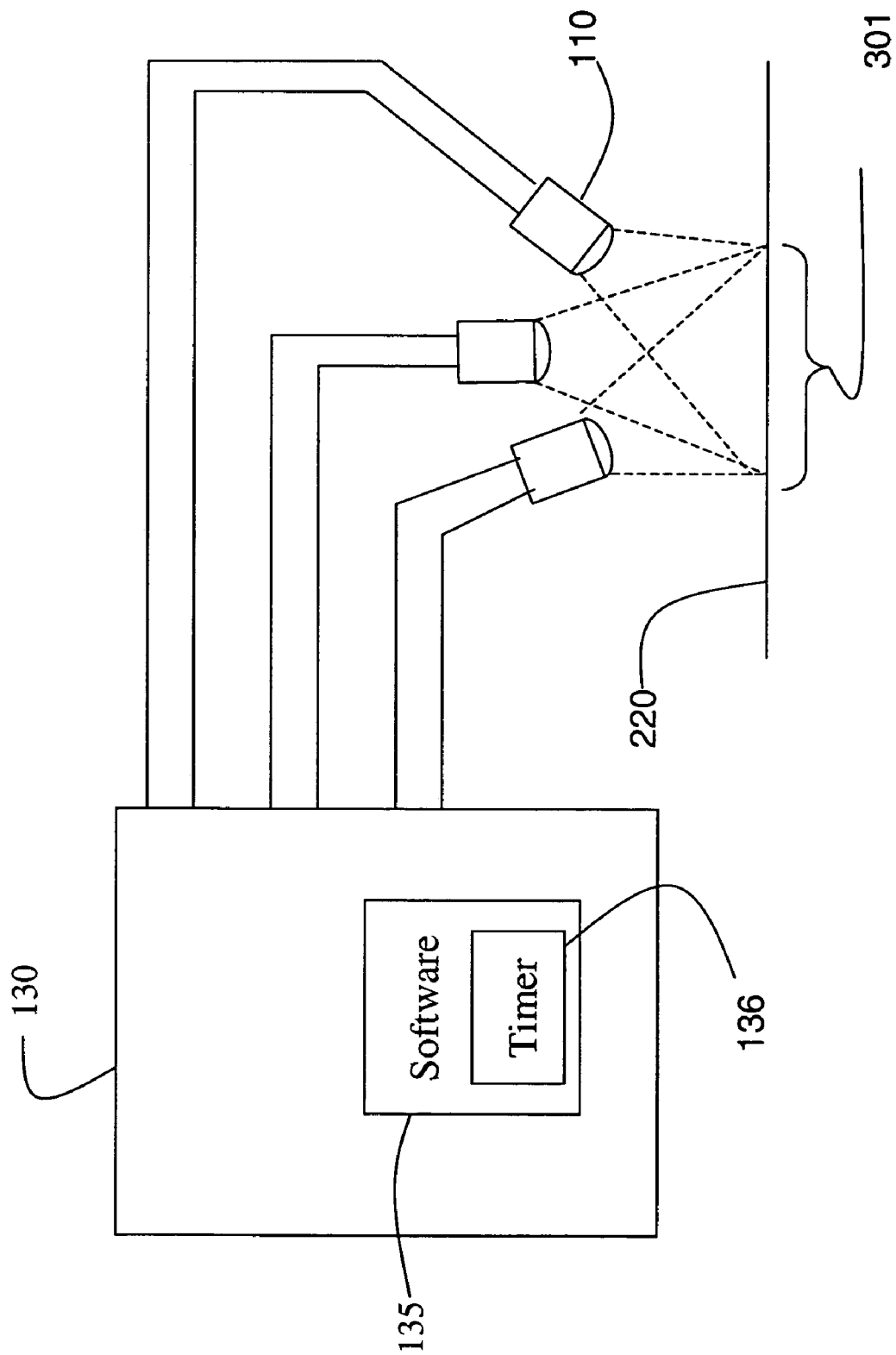
FIG. 3 is a side view of the light sensor of FIG. 2.

As shown in FIG. 3, the LEDs can be positioned so that the emitted light beams 201 are approximately aligned onto the same area 301 of the surface 220 being tested. In this configuration, the LEDs can either be placed so as to allow a specular or mirror-like reflection of the light from one LED into the other LED by having a perpendicular angle, or placed at an oblique angle so that no mirror-like reflection occurs.

This circuit can be used in two modes of operation-continuous illumination and differential illumination.

In continuous illumination, one of the LEDs emits light by setting the associated microcontroller pin connected to the LED anode to output a logic 1, and the cathode to output a logic 0. This turns the associated LED "on" in the conventional sense, and emits light along the light beam 201.

The other LEDs in the system are then utilized as described in FIG. 1. That is, the LEDs are reverse-biased to charge the internal parasitic junction capacitance, then the microcontroller pin connected to the cathode is switched to high-impedance input mode, and the time required for the capacitance to discharge due to photocurrent is measured by the microcontroller polling the input pin.

If a reproducible set of measured values are needed, then these can be produced by calibrating the system with calibration surfaces.

It should be noted that the LEDs emit relatively narrow-band light, e.g. a bandwidth of less than 50 nm. Therefore, the reflectivity of the surface, as measured by a sensing LED is the reflectivity of the surface at the wavelength emitted by an emitting LED.

By using LED that emit light at different wavelengths, the reflectivity of the surface under test can be measured.

Further, by altering the relative positions of the LEDs, with respect to each other and in respect to test surface, the reflectivity of the surface under test can be measured both in respect to the diffuse Lambertian, sometimes called 'matte' reflectivity, as well as the mirror-like, glossy, specular reflection.

Differential Measurements

In the differential mode of operation, measurements of the light levels are performed both with an LED or some other light source providing illumination to surface 220, and with no LED providing illumination to surface. The later illumination relies only on ambient natural light from the environment. A difference between the two measurements, i.e., illuminated and ambient-only, provides a way to cancel effects of changing ambient illumination, when this sequence is repeated for each measurement over time.

If in the differential mode, and the ambient and LED-illuminated measurements alternate, a fluctuating ambient source, at a similar frequencies, can interfere in the measurements. In this embodiment, whether each measurement is ambient or LED-illuminated, can be selected by a pseudo-random sequence (PRS), and averaged over a suitable time period. Any ambient interfering source that does not follow the same pseudo-random sequence is averaged out.

With a careful rearrangement, it is also possible to have all of the LEDs substantially within the domain of specular reflection of each other. In this embodiment, the system measures specular rather than diffuse reflection. This can be accomplished by placing the LEDs side by side and substantially aligned such that the limits of the light beams of each LED contain the common surface normal of each other light beam.

The advantage of this multi-channel system is that different wavelength emission LEDs can be used to obtain the surface reflectance for the set of wavelengths produced by the LEDs at the time of the measurement.

Figure 6:
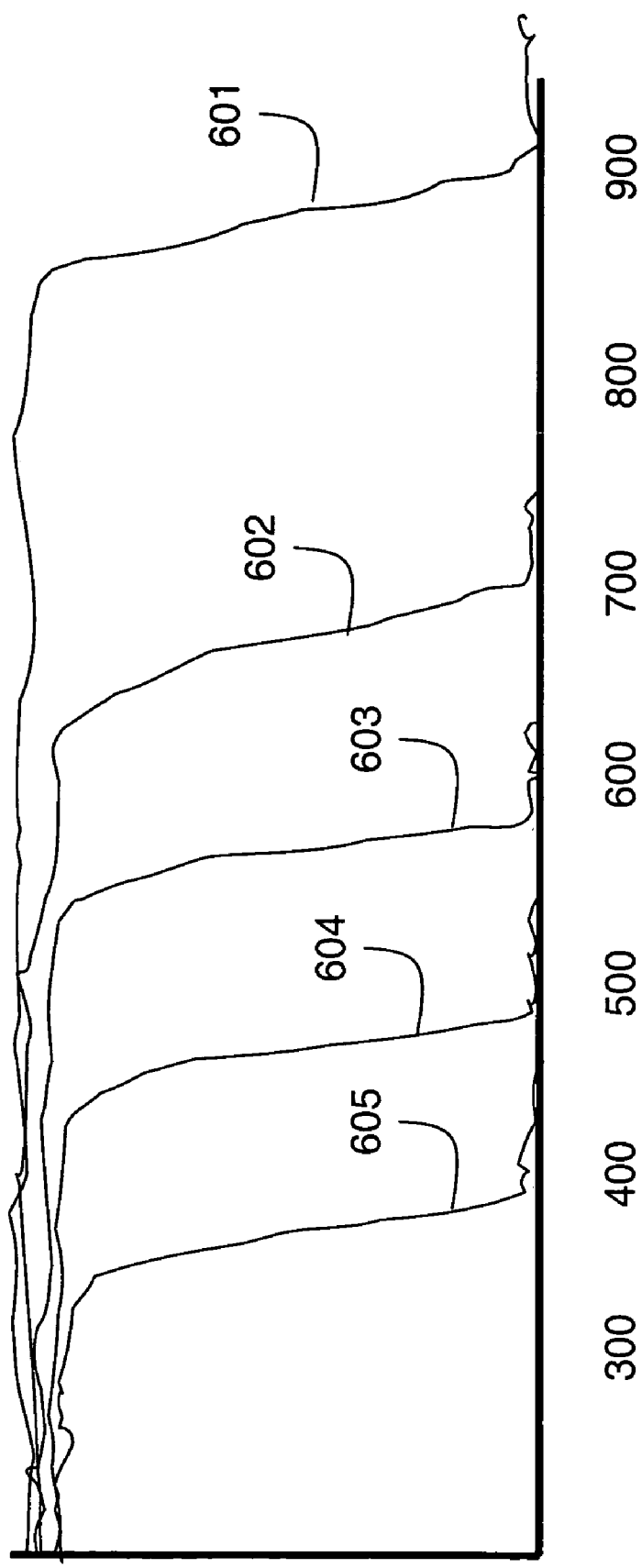
FIG. 6 is a graph of relative sensitivity of various types of LEDs indicating relative photocurrent as a function of incident light wavelength.

Because of the spectral sensitivity curve of LEDs, see FIG. 6, it is preferred to use longer-wavelength LEDs as sensors and shorter-wavelength LEDs as emitters. This is because an LED used as a sensor in the method of this invention is much more sensitive to wavelengths equal to or shorter than the emission wavelength than to wavelengths longer than the emission wavelength.

In the preferred embodiment, more than three LEDs are used. The light emitted by each LED can be sensed by any LED with an equal or longer wavelength and can act as a sensor for any other LED with an equal or shorter wavelength. As a result, having two LEDs emitting light at the very longest wavelength, such as using two infrared LEDs and a single LED of most other colors, provides the greatest span of wavelengths for sensitivity.

Sensing Transmitted Light

Figure 4A:
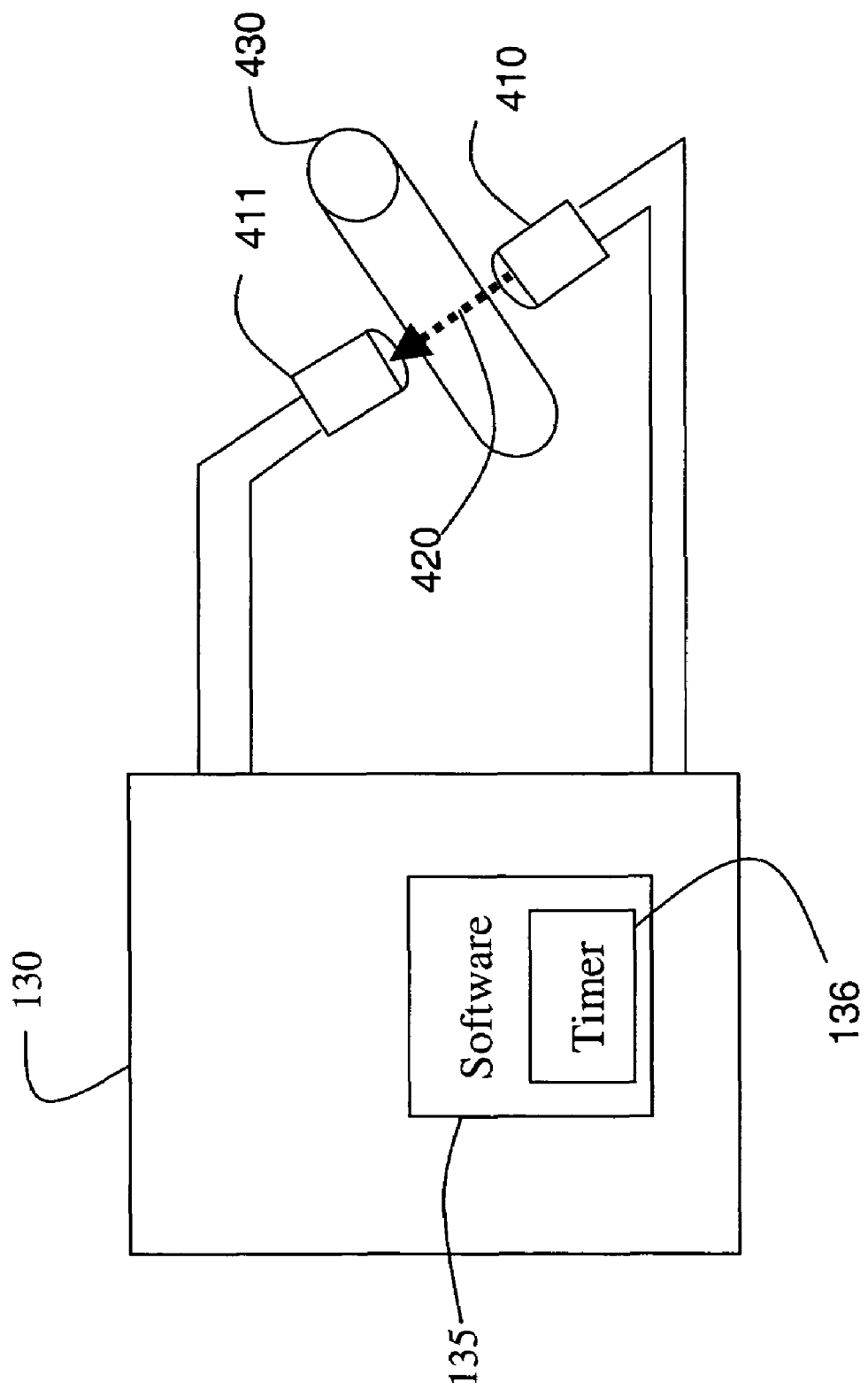
FIG. 4A is a side view of a light sensor and a test material.

FIG. 4A shows a schematic side-view of an embodiment of the invention as applied to a translucent, transparent, or opaque material between two LEDs. In this embodiment, the microcontroller 130 is connected to LEDs 410 and 411. In this arrangement of the invention, a light beam 420 that passes through a material under test 430. The material under test 430 may be a solid, a liquid, or a gas.

In this embodiment, the LED 410 emits the light beam 420. The material 430 transmits the light to some extent, acting either transparently, translucently, or opaquely to transmit, partially, or completely absorb the light beam 420. The amount of light that passes through the material is then sensed by the LED 411. This embodiment can also use the differential method described above.

Figure 4B:
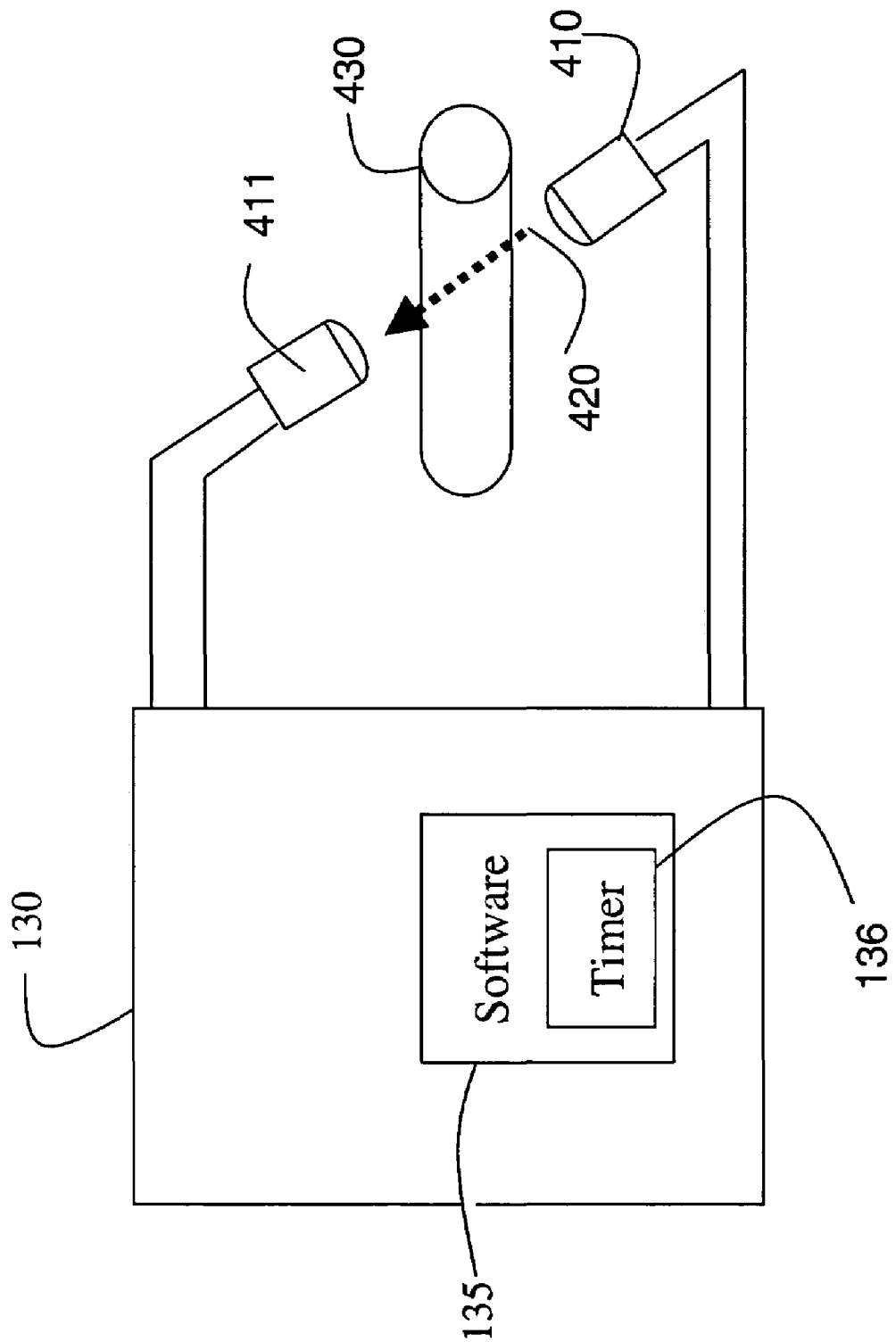
FIG. 4B is a side view of an alternate light sensor and test material.

As shown in FIG. 4B, for materials with glossy surfaces or material contained in glossy containers, the material under test 430 can be at an oblique angle with respect to the light beam 420. This eliminates spurious light measurements due to specularities.

Sensing Transmitted and Reflected Light

Figure 5A:
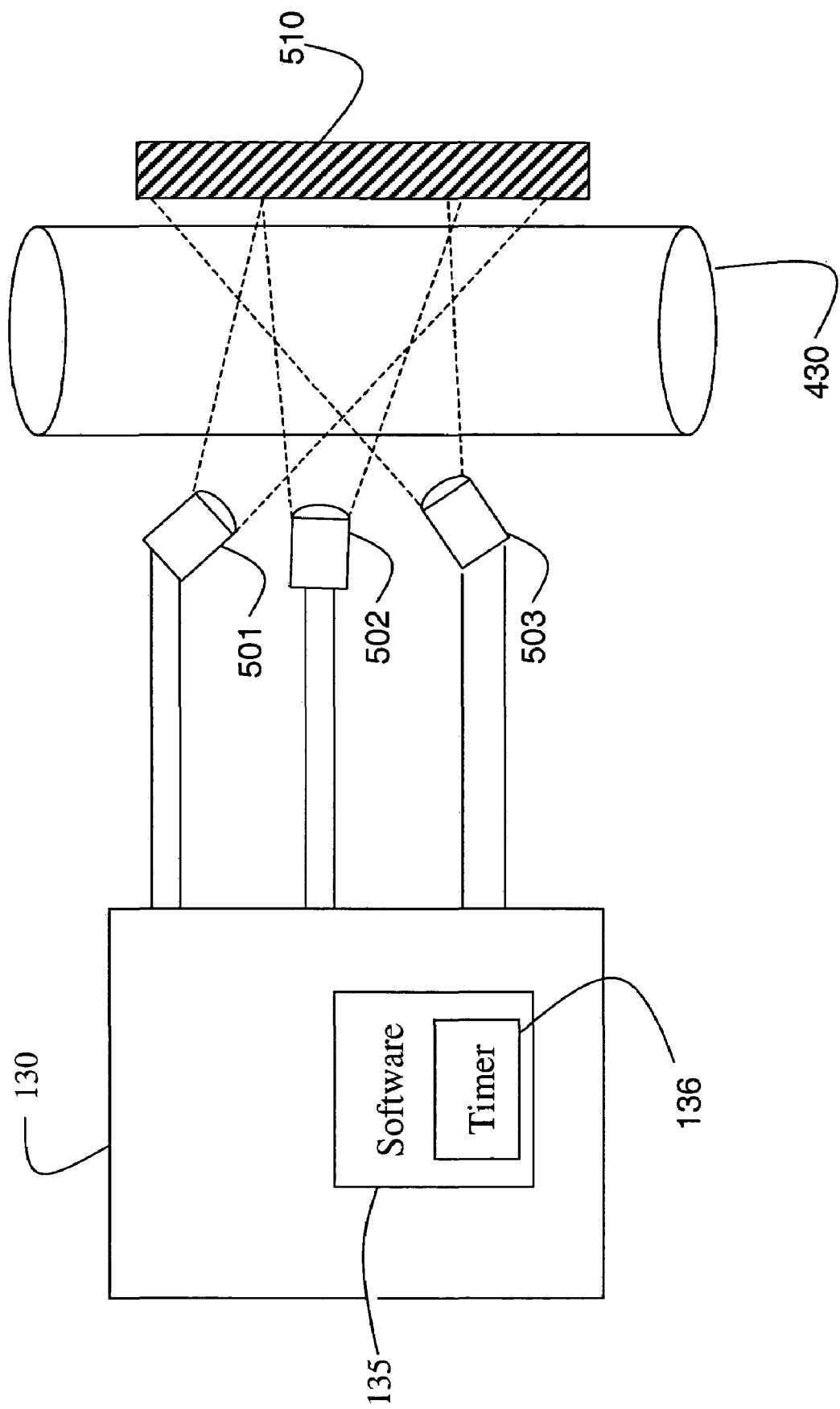
FIG. 5A is a block diagram of a light sensor for measuring specular reflection.

FIG. 5A shows an embodiment where both reflection and transmission are used. Here, the LEDs 501–503 are connected as described above. But in this embodiment, the test material 430 is placed between the LEDs 501–503 and a reflector 510 so that the incident light is perpendicular to the test material. The LEDs are positioned so that they are illuminated by specular reflection of any of the other LEDS as reflected by reflective surface 510. This way, the light passes through the material two times.

Sensing Backscatter

Figure 5B:
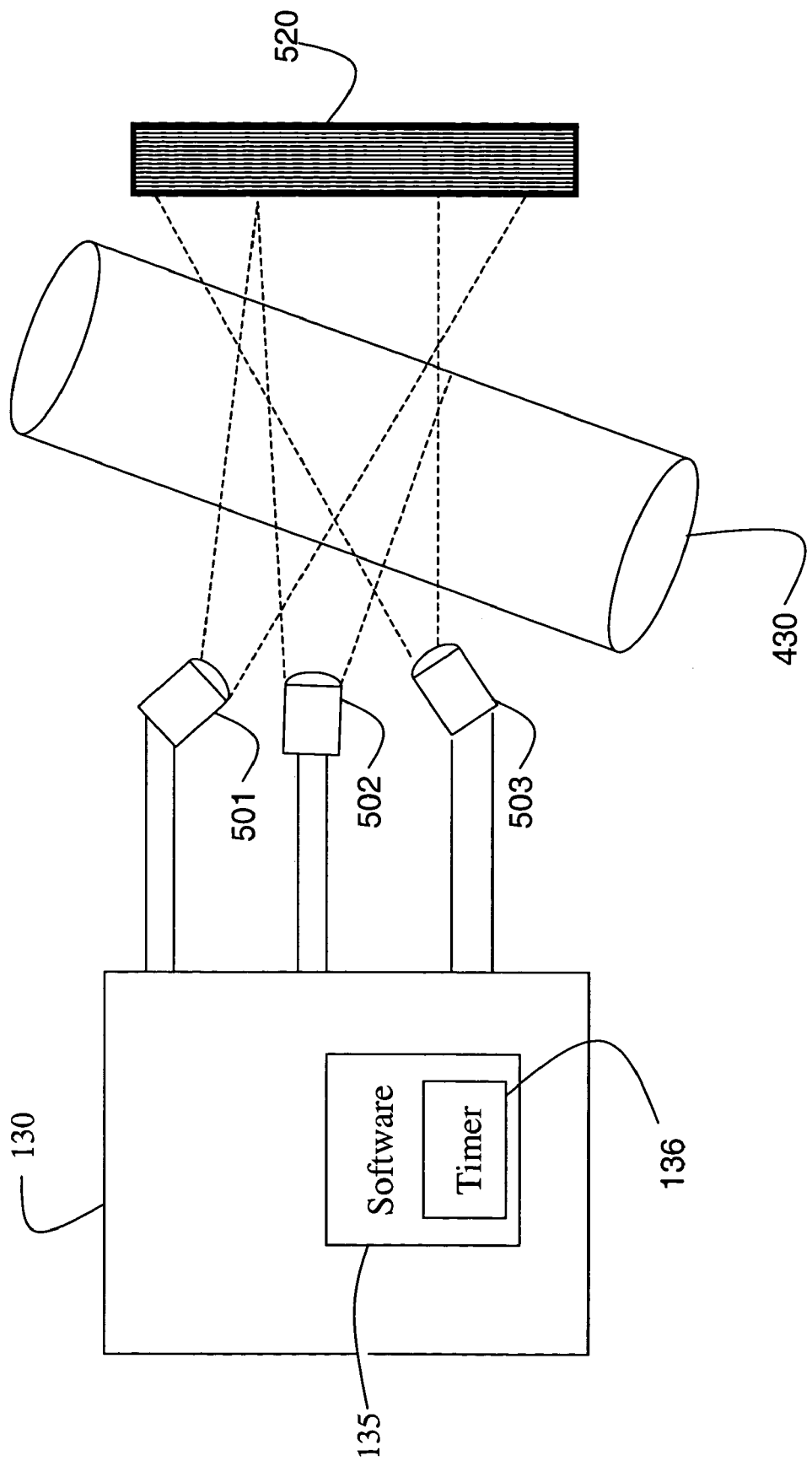
FIG. 5B is a block diagram of a light sensor for measuring diffuse reflection.

If the desired measurement is to measure the turbidity or "backscatter" within the material under test, an oblique arrangement is preferred, as shown in FIG. 5B. In this embodiment, a backing surface 520 is made of a light absorbing material that absorbs substantially all of the light passing through the material 430 under test. Additionally, note that the oblique arrangement shown in FIG. 5B causes any light reflecting from any container or glossy surface containing the material 430 is not reflected back toward the LEDs.

FIG. 6 shows typical sensitivity curves 601–605 respectively for infrared, red, yellow, blue, and ultraviolet 'colored' LEDs. when used as sensors according to the invention. The curves indicate photocurrent on the vertical axis, and wavelength in nanometers. As can be seen by a sensitivity curve 610 for a 960-nanometer (infrared) LED, the photocurrent for any wavelength in the visible region is approximately constant. As the emitting wavelength decreases, say to 588-nanometer (yellow) LED, the sensitive to yellow, blue, and ultraviolet light remains constant, but the sensitivity to red (660 nm) and orange (625 nm) light is near zero. A 470-nanometer (blue) LED is sensitive only to blue and ultraviolet light. In the general case, an LED used as a sensor according to this invention should be considered to contain an intrinsic short-wavelength-pass filter.

Figure 7:
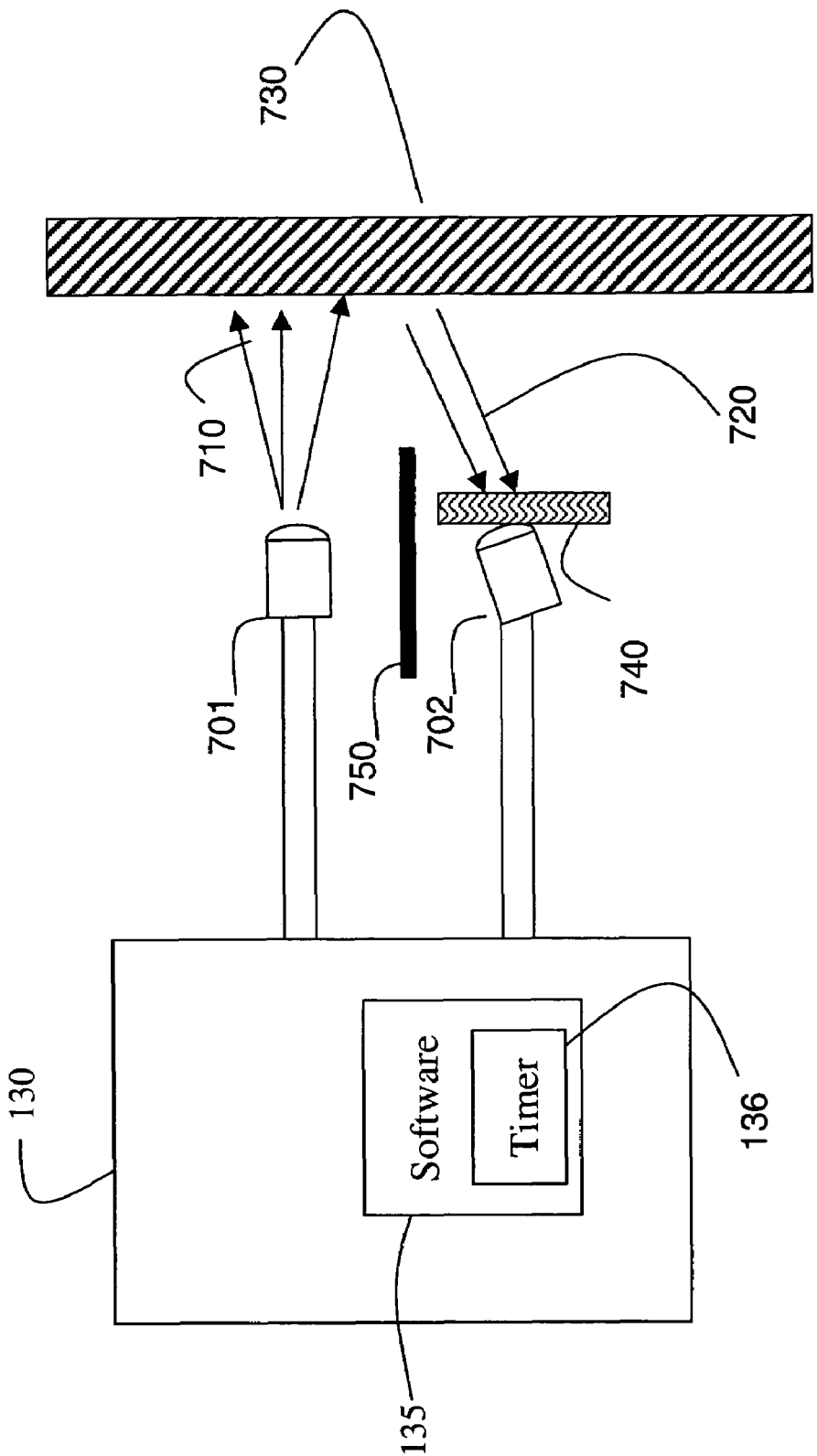
FIG. 7 is a side view of a light sensor for measuring UV fluorescence.

FIG. 7 shows a fluorescence sensor 700 according to the invention. The microcontroller 130 and LEDs 701–702 are connected as described above. The LED 701 emits 710 is an ultraviolet light 710 at 370-nanometers or shorter, such as ATX corp. type BP-200CUV750-250. The LED 701 can be connected such that it is used only for emission, and never for sensing. Also in the preferred embodiment, LED 702 is used only for sensing, and is a long-wave sensitive LED, such as a 950-nanometer (infrared) or 639-nanometer (red) LED.

LED 701 is arranged so that the emitted UV light 710 illuminates fluorescent material 730. The fluorescent material fluoresces under the ultraviolet light and emits visible light 720. The visible light 720 passes through a UV-blocking filter 740 and is detected by LED 702 in the manner described above. An opaque light shield 750 prevent any of the emitted UV light 710 from being sensed directly by the sensor LED 702.

Although the invention has been described by way of examples of preferred embodiments, it is to be understood that various other adaptations and modifications may be made within the spirit and scope of the invention. Therefore, it is the object of the appended claims to cover all such variations and modifications as come within the true spirit and scope of the invention.

I claim:

1. A light sensor comprising:
   a set of light emitting diodes, each light emitting diode configured to emit a corresponding wavelength such that at least one wavelength of one light emitting diode is different than one other wavelength of another light emitting diode; and
   a microcontroller, comprising:
   a plurality of pairs of I/O pins, there being one pair of I/O pins connected to one corresponding light emitting diode;
   means for selectively driving a first subset of the light emitting diodes in a reverse bias to charge a capacitance of the first subset of light emitting diodes; and
   means for measuring a time for the capacitance of each of the first subset of light emitting diodes to discharge due to photocurrent induced by incident light on the first subset of light emitting diodes, the time being inversely proportional to an intensity of the incident light.

2. The light sensor of claim 1, in which the incident light is ambient natural light.

3. The light sensor of claim 1, in which the incident light is emitted by an external light source.

4. The light sensor of claim 1, further comprising:
   means for selectively driving a second subset of the set of light emitting diodes in a forward bias to emit light at the corresponding wavelengths, while driving the first subset of light emitting diodes in the reverse bias so that the incident light emitted by the second subset of light emitting diodes is detected by the first subset of light emitting diodes.

5. The light sensor of claim 1, further comprising:
   a capacitance connected in parallel with each light emitting diodes.

6. The light sensor of claim 1, in which the means for measuring uses a logic level threshold of the microcontroller.

7. The light sensor of claim 1, in which the means for measuring includes a interrupt service procedure.

8. The light sensor of claim 1, in which the means for measuring includes a polling procedure.

9. The light sensor of claim 1, in which the means for measuring includes a clock of the microcontroller.

10. The light sensor of claim 1, in which the capacitance is a parasitic capacitance inherent in the light emitting diodes, the microcontroller I/O pins, and connective wiring.

11. The light sensor of claim 10, in which the parasitic capacitance is about twenty picofarads.

12. The light sensor of claim 1, in which the capacitance is charged by configuring the corresponding I/O pins in output mode.

13. The light sensor of claim 1, in which the capacitance is discharged by configuring the corresponding I/O pins in input mode.

14. The light sensor of claim 13, in which an impedance of the corresponding pins configured in the input mode is greater than a million Ohms.

15. The light sensor of claim 1, in which the means for measuring produces directly a pulse-width-modulated logic-level signal with a width of the pulse being inversely proportional to the intensity of the incident light.

16. The light sensor of claim 1, further comprising:
   a test material to reflect the incident light.

17. The light sensor of claim 4, further comprising:
   a test material to transmit the incident light.

18. The light sensor of claim 16, in which a surface of the test material is placed at a perpendicular angle with respect to the incident light to measure specular reflectance.

19. The light sensor of claim 16, in which a surface of the test material is placed at an oblique angle with respect to the incident light to measure diffuse reflectance.

20. The light sensors of claim 4, further comprising:
   means for alternating the driving of the first subset of light emitting diodes and the second subset of light emitting diode in the reverse and forward bias.

21. The light sensor of claim 1, in which the incident light includes ambient light and light from a light source, and further comprising:
    means for measuring a difference between an intensity of the ambient light, and an intensity of the light from the other light source to enable a differential measuring of the intensity of the incident light.

22. The light sensors of claim 4, further comprising:
    means for continuously driving the first subset and the second subset in the forward and reverse bias, respectively.

23. The light sensors of claim 1, further comprising:
    means for selecting the light emitting diodes in the first and second subset by a pseudo-random sequence; and
    means for averaging the measured times while selecting according to the pseudo-random sequence.

24. The light sensor of claim 4, in which the wavelengths of the first set of light emitting diodes is less than or equal to the wavelengths of the second set of light emitting diodes.

25. The light sensor of claim 1, further comprising:
    a test material placed between the incident light and the first subset of light emitting diodes so that the incident light passes through the test material to measure the intensity of the incident light transmitted through the test material.

26. The light sensor of claim 24, in which the test material is placed at a perpendicular angle with respect to the incident light.

27. The light sensor of claim 24, in which the test material is placed at an oblique angle with respect to the incident light.

28. The light sensor of claim 24, in which the test material is translucent.

29. The light sensor of claim 24, in which the test material is opaque.

30. The light sensor of claim 4, in which a test material is placed between a reflector and the first and second sets of light emitting diodes.

31. The light sensor of claim 28, in which the test material is at a perpendicular angle with respect to the incident light.

32. The light sensor of claim 28, in which the test material is at an oblique angle with respect to the incident light to measure turbidity within the test material.

33. The light sensor of claim 4, in which the second set of light emitting diodes emit ultraviolet light as the incident light.

34. The light sensor of claim 31, in which the incident light is reflected from a fluorescent test material to the first set of light emitting diodes.

35. A method for sensing incident light, comprising the steps of:
    selecting a set of light emitting diodes having corresponding wavelengths such that at least one wavelength of one light emitting diode is different than one other wavelength of another light emitting diode; and
    selectively driving a first subset of the light emitting diodes in a reverse bias to charge a capacitance of the first subset of light emitting diodes; and
    measuring a time for the capacitance of each of the first subset of light emitting diodes to discharge due to photocurrent induced by incident light on the first subset of light emitting diodes, the time being inversely proportional to an intensity of the incident light.

36. The method of claim 33, further comprising:
    selectively driving a second subset of the set of light emitting diodes in a forward bias to emit light at the corresponding wavelengths, while driving the first subset of light emitting diodes in the reverse bias so that the incident light emitted by the second subset of light emitting diodes is detected by the first subset of light emitting diodes.

37. The method of claim 33, in which a test material reflects the incident light.

38. The method of claim 33, in which a test material transmits the incident light.

39. The method of claim 34, further comprising:
    placing a test material between the first set and the second set of light emitting diodes.

* * * * *